(12) United States Patent
Mukerjee et al.

(10) Patent No.: US 7,753,888 B2
(45) Date of Patent: Jul. 13, 2010

(54) METHOD AND/OR APPARATUS FOR PUNCTURING A SURFACE FOR EXTRACTION, IN SITU ANALYSIS, AND/OR SUBSTANCE DELIVERY USING MICRONEEDLES

(75) Inventors: Erik V. Mukerjee, San Ramon, CA (US); Rosemary L. Smith, Bangor, ME (US)

(73) Assignee: The Regents of the University of California

( * ) Notice: Subject to any disclaimer, the term of this patent is extended or adjusted under 35 U.S.C. 154(b) by 1055 days.

(21) Appl. No.: 10/995,570

(22) Filed: Nov. 22, 2004

(65) Prior Publication Data
US 2005/0171480 A1    Aug. 4, 2005

Related U.S. Application Data

(60) Provisional application No. 60/524,296, filed on Nov. 21, 2003.

(51) Int. Cl.
*A61M 5/00* (2006.01)
(52) U.S. Cl. .................................................. 604/173
(58) Field of Classification Search .............. 604/173, 604/272
See application file for complete search history.

(56) References Cited

U.S. PATENT DOCUMENTS

| | | | |
|---|---|---|---|
| 3,964,482 A | 6/1976 | Gerstel et al. | |
| 4,018,938 A | 4/1977 | Feder | |
| 4,165,395 A | 8/1979 | Chang | |
| 4,523,807 A | 6/1985 | Suzuki | |
| 5,389,954 A | 2/1995 | Inaba | |
| 5,543,108 A | 8/1996 | Bacher | |
| 5,928,207 A | 7/1999 | Pisano | |
| 6,093,520 A | 7/2000 | Vladimirsky | |
| 6,132,755 A | 10/2000 | Eicher | |
| 6,406,638 B1 | 6/2002 | Stoeber | |
| 6,537,264 B1 | 3/2003 | Cormier | |
| 6,558,361 B1 * | 5/2003 | Yeshurun | 604/272 |
| 6,603,987 B2 | 8/2003 | Whitson | |
| 6,689,100 B2 | 2/2004 | Connelly | |
| 6,749,792 B2 | 6/2004 | Olson | |
| 6,881,203 B2 | 4/2005 | Delmore | |
| 6,908,453 B2 | 6/2005 | Fleming | |
| 6,962,772 B2 | 11/2005 | Liu | |

(Continued)

FOREIGN PATENT DOCUMENTS

WO    WO/2005/060621    7/2005

OTHER PUBLICATIONS

Clague, David, "Simulation-Aided Design of Microfluidic Devices"; Lawrence Livermore National Laboratory, pp. 4-11, Dec. 2001.

(Continued)

*Primary Examiner*—Kevin C Sirmons
*Assistant Examiner*—Elizabeth R Moulton
(74) *Attorney, Agent, or Firm*—Quine Intellectual Property Law Group; Stephen J. LeBlanc

(57) ABSTRACT

A method and apparatus for puncturing a surface for extraction, in situ monitoring, and/or substance delivery uses microneedles with improved properties. Applications include easy to handle glucose monitoring using a group of hollow out-of-plane silicon microneedles to sample substances in interstitial fluid from the epidermal skin layer.

21 Claims, 11 Drawing Sheets

U.S. PATENT DOCUMENTS

| | | |
|---|---|---|
| 7,025,774 B2 | 4/2006 | Freeman |
| 7,108,681 B2 * | 9/2006 | Gartstein et al. ............ 604/173 |
| 2002/0045859 A1 * | 4/2002 | Gartstein et al. ............ 604/117 |
| 2002/0133129 A1 | 9/2002 | Arias |

OTHER PUBLICATIONS

Kuo et al., "A Novel Polymer Microneedle Arrays and PDMS Micromolding Technique", Tamkang Journal of Science and Engineering, vol. 7, No. 2 pp. 95-98 (2004).

* cited by examiner

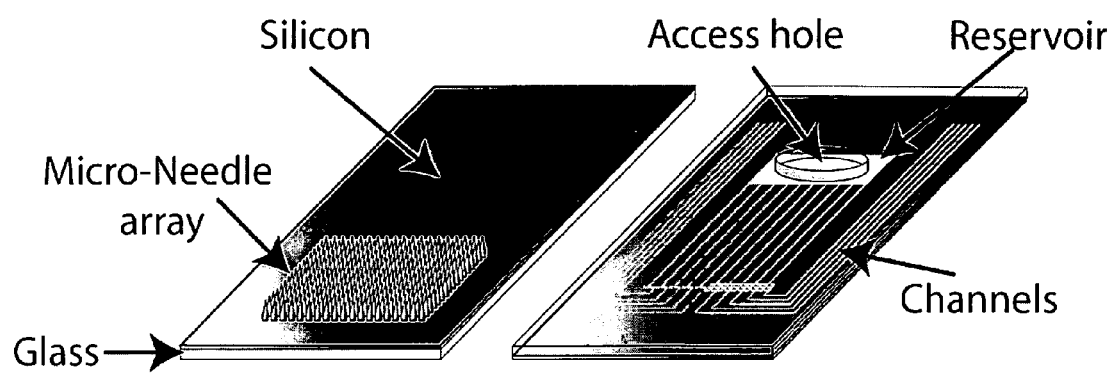
*FIG. 9*
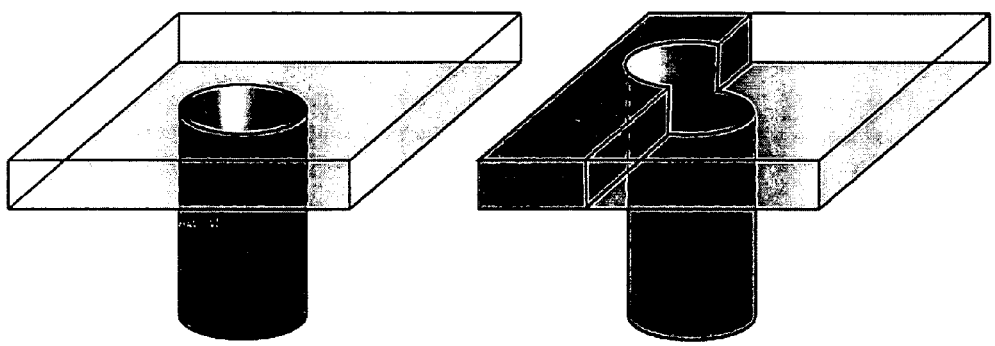
*FIG. 10A*   *FIG. 10B*

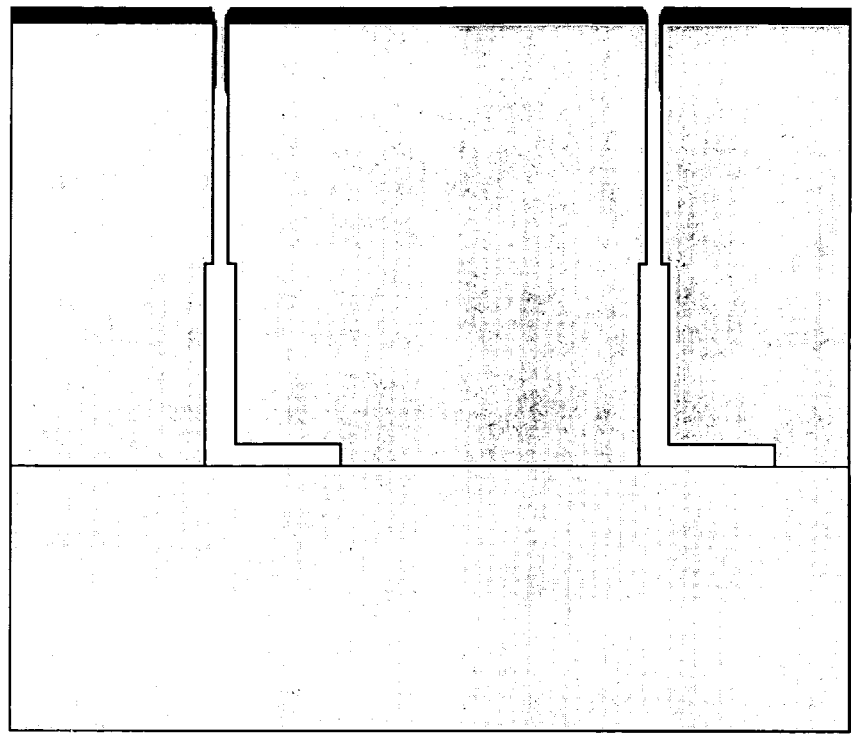
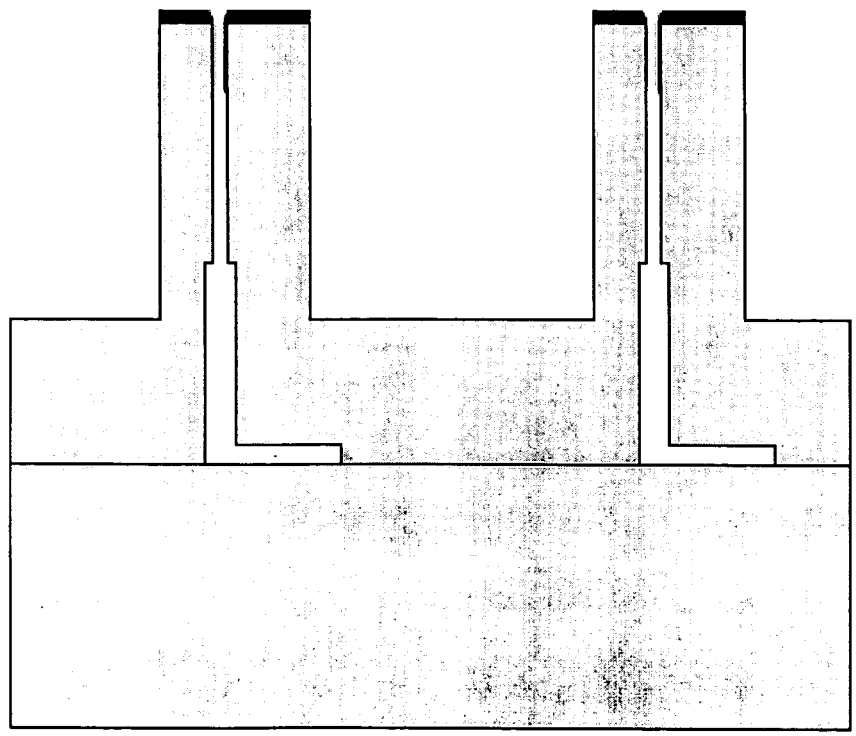
*FIG. 12*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 14. (TABLE 1)*

METHOD AND/OR APPARATUS FOR PUNCTURING A SURFACE FOR EXTRACTION, IN SITU ANALYSIS, AND/OR SUBSTANCE DELIVERY USING MICRONEEDLES

CROSS REFERENCE TO RELATED APPLICATIONS

This application claims priority from provisional patent application 60/524,296 filed 21 Nov. 2003 and incorporated herein by reference.

The Invention was made with government support under Grant (Contract) No. N66001-01-8001 awarded by the Department of Defense. The Government has certain rights to this invention.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

A minimally invasive method for sampling biological fluids is a prerequisite to performing either periodic or continuous monitoring of physiological systems. Furthermore, minimally invasive methods of delivering drugs or other substances, painlessly and optionally continuously and optionally in combination with monitoring, a timer, or other means for automatically determining when to administer the substance, would be useful in many treatment applications. In particular, blood and cellular interstitial fluid (ISF) contain important metabolic and immunological biomolecules whose time varying concentrations are important indicators of various states of health and disease. The transdermal sampling of small volumes of blood for glucose concentration measurement is part of the daily routine for many diabetic patients to monitor and control the symptoms of their disease. Although they are considered minimally invasive techniques, needle pricks and lancets do produce tissue damage and patient discomfort. The use of microtechnology to reduce the size of needles to minimize discomfort is a rapidly developing arena of investigation for the transcutaneous delivery of drugs.

The epidermis forms the outermost skin barrier. It is relatively impermeable to both polar and non-polar lipophilic molecules. Its outermost layer, the stratum corneum, varies in thickness from 10-40 microns and consists of adherent dead cells, with thickened, cross-linked sub-plasma membrane protein "envelopes" encased in pericellular lipids. The epidermis, which varies in thickness from 50-100 microns, sits atop the lower layer of the skin, the dermis, from which it is separated by a proteinaceous basement membrane. Blood vessels and capillaries lie in the dermis. The epidermis is devoid of blood vessels and receives its nourishment by diffusion from the capillaries that lie in the superficial dermis directly beneath the dermo-epidermal junction. It is this area that is optimally targeted for ISF extraction-superficial enough to be painless, yet in close proximity to capillary blood flow for monitoring equilibrating constituents of interest (e.g. glucose).

Despite recent advances in the configuration and/or fabrication of semiconductor-based or other microneedles, there still exits a need for improved needle designs.

SUMMARY

The present invention involves improved micro-needles. Specific embodiments involve microneedles with substantially solid tips, where an opening to an underlying channel is nearer to the base of the needle. Needles and associated structures and methods according to specific embodiments of the invention provide mechanisms for detecting and/or monitoring substances of interest or delivering drugs or other substances of interest through surfaces, particularly in biological research and/or clinical settings. In specific embodiments, the invention involves methods and devices related to improved micro-needle fabrication, in particular in semiconductor materials, though optionally using other materials.

In more specific embodiments, the invention involves a method and/or apparatus for delivering material or sampling material under the skin of a human or animal or under the outer layer of a plant using out-of-plane microneedles with improved configurations. For humans and animals, this can allow painless everyday usage for monitoring and/or delivery. In other embodiments the invention relates generally to a method and apparatus for continuous monitoring or delivery of compounds in the epidermal interstitial fluid. In further specific embodiments, the invention involves an array (used herein to indicate any type of grouping) of out-of-plane microneedles that can effectively penetrate a skin or other surface.

In specific applications, microneedles according to specific embodiments of the invention can be used along with other disclosed methods and devices for substance monitoring and delivery in research, diagnostic, or treatment applications, such as discussed herein and in documents cited herein and/or incorporated herein by reference.

In specific embodiments, the invention involves a hollow microneedle array with integrated, fluidic microchannels in which the ability to extract interstitial fluid from human skin has been demonstrated. Filling of the integrated microchannels by capillary action with both non-biological fluids (glycerol, ethanol, surrogate interstitial fluid (ISF) and water) as well as biological fluids (ISF and whole blood) has been achieved. In specific embodiments, a microneedle array is integrated with connecting microchannels and a common reservoir, creating a generic platform, which is suitable for the inclusion of microsensors and microfluidic control devices. In specific embodiments, microneedles according to the invention can be configured in a disposable sensor and/or substance delivery system that is minimally invasive and provides accurate sensor readings and painless and easy sensor application. An example of such a system consists of hollow out-of-plane microneedles to sample glucose from the interstitial fluid of the epidermis, a micro-fluidic channels and sensors.

In further embodiments, fabrication methods and an approach are disclosed in which the same series of fabrication steps and lithographic masks can create a wide range of needle sizes and shapes that can be custom built for different applications. In further specific embodiments, these fabrication methods are used to achieve optimal tip shape, opening size, needle height and needle area density for use in particular applications.

While needles according to specific embodiments of the present invention are described herein as used for performing a biological assay or delivering substances of interest to humans or animals, it will be understood to those of skill in the art that in specific embodiments, the invention can be used in a variety of applications. These applications include, but are not limited to: detecting contaminants in foodstuffs;

detecting ripeness and/or the presence of sugars in plants or plant parts; detecting the presence of a desired substance (such as petroleum components) in an exploration operation; insuring the presence of desired elements in a manufacturing product, etc.

The invention and various specific aspects and embodiments will be better understood with reference to drawings and detailed descriptions provided in this submission. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of devices and/or systems that include different innovative components and innovative combinations of innovative components and known components. No inference should be taken to limit the invention to combinations containing all of the innovative components listed in any illustrative embodiment in this specification.

In some of the drawings and detailed descriptions below, the present invention is described including various parameters of dimension and/or other parameters. These should be understood as illustrating specific and possible preferred embodiments, but are not intended to limit the invention. Many devices and/or methods have variations in one or more of the detailed parameters described herein will be apparent to persons of skill in the art having the benefit of the teachings provided herein and these variations are included as part of the present invention.

All references, publications, patents, and patent applications cited and/or provided with this submission are hereby incorporated by reference in their entirety for all purposes.

BRIEF DESCRIPTION OF THE DRAWINGS

FIG. 9 illustrates one example of a complete transdermal fluid transport device with approximately 400 microneedles and other components according to specific embodiments of the present invention.

FIG. 10A-B illustrates an example showing uncompensated and compensated through-hole reservoir interface according to specific embodiments of the present invention.

FIG. 12 is a schematic diagram illustrating additional fabrication steps involving capping for forming microneedles according to specific embodiments of the invention.

FIG. 14 (Table 1) illustrates an example of diseases, conditions, or statuses for which substances of interest can evaluated according to specific embodiments of the present invention.

DESCRIPTION OF SPECIFIC EMBODIMENTS

1. Definitions

Figure 1:
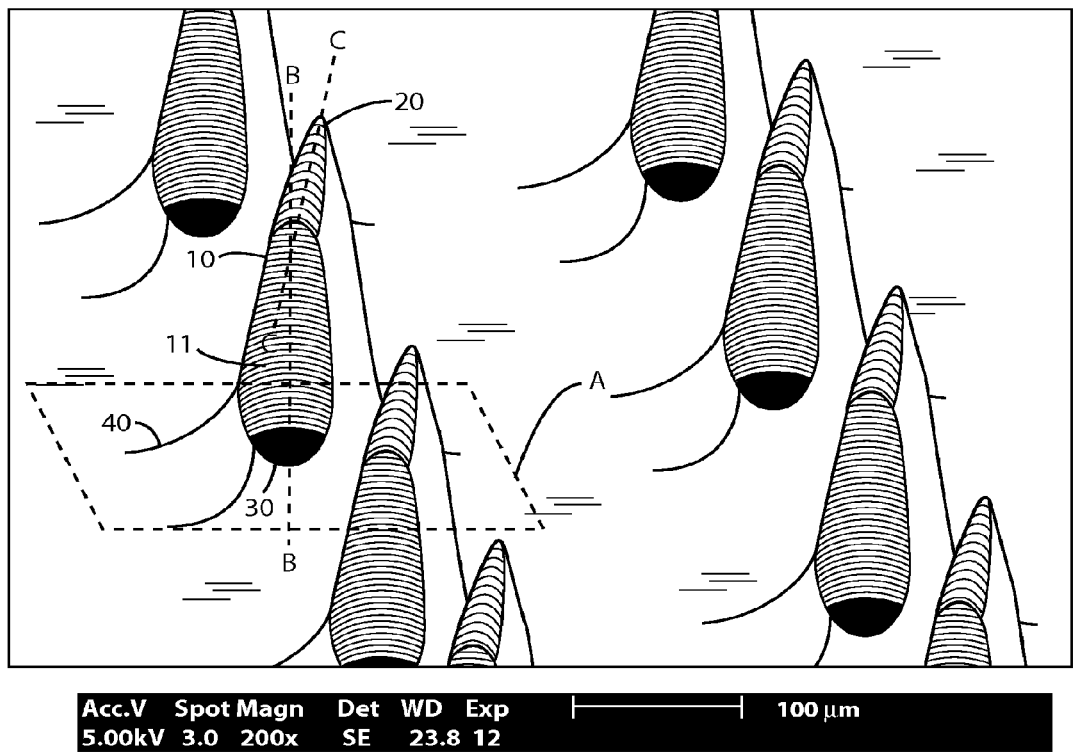
FIG. 1 is micrograph of an example snake-fang microneedle array according to specific embodiments of the invention.

The following definitions may be used to assist in understanding this submission. These terms, as well as terms as understood in the art should be used as a guide in understanding descriptions provided herein.

A "substrate" is a, preferably solid, material suitable for the attachment or forming of one or more structures or channels as described herein. Substrates can be formed of materials including, but not limited to glass, plastic, silicon, germanium, minerals (e.g. quartz), semiconducting materials (e.g. silicon, germanium, etc.), ceramics, metals, etc.

2. Overview

The present invention involves methods, devices, and systems that enable improved sampling of substances of interest and/or improved delivery of drugs or other substances through a surface (such the skin or outer layer of a plant, animal, or organ or part thereof) by using out-of-plane microneedles. Although a standard metal hypodermic needle is effective in piercing the outer layer of skin (e.g., stratum corneum) and accessing the tissue and blood vessels beneath it for monitoring, sampling or delivery, interfacing a standard sized needle with a silicon microchip is a challenging problem of scale. Larger needles also create discomfort and safety issues when used in various research and/or treatment settings.

Great reduction in needle size creates a number of problems. Microneedles of various heights, (e.g. for humans, with a shank height in the range of about 150-350 microns) have been proposed for various monitoring or delivery applications. However, even very sharp microneedles often fail to pierce skin or other biological surfaces due to the soft underlying tissue and the elastic nature of the skin that can result in bending and folding around the needle tip to a depth greater than the needle shank height. If the microneedles are made taller, but of the same diameter, they tend to bend (buckle) at pressures less than that required to pierce the desired surface, e.g., the tough stratum corneum of many areas of the human skin.

Due to the very small needle openings of many proposed hollow microneedles, tips may also clog. This is especially problematic if the opening is at or very near the apex (or tip) of the needle. These problems are solved with specific embodiments of microneedles and/or systems and/or methods of the present invention as described herein.

Mammalian skin can be categorized into two distinct layers. In humans, the surface layer (epidermis) is primarily made up of 100 micron-2 mm thick layer of epithelial cells.

The underlying layer (dermis) typically includes a 1.1 mm layer of connective tissue. Skin thickness varies at different locations of the body as well as epidermal/dermal proportions. For example, the epidermis is extremely thick (400-600 microns) on the palms of the hand and soles of the feet, whereas the dermis is thickest near the upper back (1.1 mm). The epidermis itself lacks blood vessels and draws nourishment by diffusion from vessels located 200-500 microns away in the underlying dermis. Although free nerve endings are present in the epidermis, experiments have shown that breaching the epidermis generally causes no or very little pain.

A minimally invasive method for sampling biological fluids is a prerequisite to performing either periodic or continuous monitoring of physiological systems. Blood and cellular interstitial fluid (ISF) contain important metabolic and immunological biomolecules. The time varying concentrations of these molecules are important indicators of various states of health and disease. The transdermal sampling of small volumes of blood for glucose concentration measurement is part of the daily routine for many diabetic patients to monitor and control the symptoms of their disease. The use of microtechnology to reduce the size of needles to minimize discomfort is a rapidly developing arena of investigation for the transcutaneous delivery of drugs. However, despite the rapid advances in lab-on-a chip technology that can separate, concentrate and analyze biological indicators, the ability to deliver minute biological samples to the microchip for analysis requires further development. A few demonstrations of transdermal biological fluid extraction and analysis using microfabricated devices and have been reported, using microneedles and thermal ablation.

Although a standard metal hypodermic needle is quite effective in piercing the stratum corneum, and accessing the tissue and blood vessels beneath it, interfacing a standard sized needle with a silicon microchip is a challenging problem of scale. Creating a micro-miniature version of this structure presents not only a less invasive and less painful extraction method, but also enables the integration of the sample delivery device with analysis system. However, great reduction in size creates some new problems. Even experimentation using very sharp microneedles with a tip radius of curvature less than 2 microns often fail to pierce skin because of the soft underlying tissue and the elastic nature of the skin, which can bend and fold around the needle tip to a depth greater than the needle shank height. If the needles are made taller, but of the same diameter, they tend to bend (buckle) at pressures less than that required to pierce the tough stratum corneum of the skin. Another problem is tip clogging, due to the very small needle openings. This is especially problematic if the opening is at the apex of the needle, because it is forced into the skin.

A number of techniques for forming needles from semiconductors or other materials that can be similarly etched or molded have been discussed. For example, U.S. Pat. No. 6,406,638, by inventors Boris Stoeber and Dorian Liepmann and assigned to The Regents of the University of California (Oakland, Calif.), entitled "Method of forming vertical, hollow needles within a semiconductor substrate, and needles formed thereby" discusses forming a needle by anisotropically etching a channel into the back side of a semiconductor substrate with the front side of the semiconductor substrate then isotropically etched to form a vertical axial surface surrounding the channel. Co-assigned U.S. Pat. No. 5,928,207, invented by Albert P. Pisano and Kyle S. Lebouitz, and entitled "Microneedle with Isotropically Etched Tip, and Method of Fabricating such a Device", uses isotropic etching to form microneedles in the horizontal plane of a semiconductor substrate. Another semiconductor fabrication technique for forming needles is discussed by Neil H. Talbot, Christopher G. Keller, and Albert P. Pisano, in their U.S. patent application Ser. No. 09/044,398, filed Mar. 18, 1998, entitled "Apparatus and Method for Fabricating Needles Via Conformal Deposition in Two-Piece Molds". This technology forms a needle via conformal deposition within a horizontally-oriented chamber defined by a two-piece mold.

REFERENCES

A number of references may be considered relevant to the present invention or provide background material or details regarding methods known in the art that may have relevance to specific embodiments of the invention. The following as well as any publications cited herein are hereby incorporated by reference for all purposes.

[1] S. Henry, D. V. McAllister, M. G. Allen, M. R. Prausnitz, Microfabricated microneedles: a novel approach to transdermal drug delivery, J. Pharm. Sci. 87 (1998) 922-925.

[2] E. T. Lagally, C. A. Emrich, R. A. Mathies, Fully integrated PCRcapillary electrophoresis microsystem for DNA analysis, Lab Chip 1 (2001) 102-107.

[2] J. Liu, K. Tseng, B. Garcia, C. B. Lebrilla, E. Mukerjee, S. Collins, R. Smith, Electrophoresis separation in open microchannels. A method for coupling electrophoresis with MALDI-MS, Anal. Chem. 73 (2001) 2147-2151.

[4] N. Szita, J. Dual, and R. Buser. An actuation coupling system for a fast and low volume micropipetting device with integrated sensors, presented at ACTUATOR 2000, 7th International Conference on New Actuators and International Exhibition on Smart Actuators and Drive Systems, Conference Proceedings. MESSE BREMEN GMBH, Bremen, Germany, 2000, pp.228-231.

[5] S. R. Visuri, K. Ness, J. Dzenitis, B. Benett, K. Bettencourt, J. Hamilton, K. Fisher, and P. Krulevitch. Microfluidic tools for biological sample preparation, presented at 2nd Annual International IEEE-EMBS Special Topic Conference on Microtechnologies in Medicine and Biology, Proceedings (Cat. No.02EX578). IEEE, Piscataway, N.J., USA, 2002, pp.556-559.

[6] W. H. Smart, K. Subramanian, The use of silicon microfabrication technology in painless blood glucose monitoring, Diabetes Technol. Therapeutics 2 (2000) 549-559.

[7] J. G. E. Gardeniers, J. W. Berenschot, M. J. de Boer, Y. Yeshurun, M. Hefetz, R. van't Oever, and A. van den Berg, Silicon micromachined hollow microneedles for transdermal liquid transfer, presented at MEMS 2002 IEEE International Conference, Fifteenth IEEE International Conference on Micro Electro Mechanical Systems (Cat. No.02CH37266) Technical Digest. MEMS 2002 IEEE International Conference, Fifteenth IEEE International Conference on Micro Electro Mechanical Systems, Las Vegas, Nev., USA, 2002.

[8] P. Griss, G. Stemme. Novel, side opened out-of-plane microneedles for microfluidic transdermal interfacing, presented at MEMS 2002 IEEE International Conference, Fifteenth IEEE International Conference on Micro Electro Mechanical Systems (Cat. No.02CH37266) Technical Digest. MEMS 2002 IEEE International Conference. Fifteenth IEEE International Conference on Micro Electro Mechanical Systems, Las Vegas, Nev., USA, 2002.

[9] S. Chandrasekaran, J. Brazzle, and A. B. Frazier, Surface Micromachined Metallic Microneedles, J. Microelectromechan. Syst. 12 (2003) 281-288.

3. Example Needle Configurations

According to various embodiments, three different configurations for microneedles are disclosed. Each shape represents separate embodiments with different advantages in different applications. In specific embodiments, combinations of needle types may be used for particular applications. In further embodiments, a microneedle array includes some solid and some hollow needles to improve mechanical aspects of needle performance.

Microneedle with Substantially Solid Tip and Off-center Through-hole

One advantageous shape for a microneedle according to specific embodiments of the invention, in particular for many animal and human applications is a microneedle with a substantially solid tip and off-center through-hole. Such a structure may be characterized by a substantially solid tip or needle-shaft apex, with a through-hole that fully opens a substantial distance below the tip, but the opening of which can include a grooved extending from somewhat below the tip to the top of the off-center through-hole. Characterization studies have shown that this needle configuration results in superior puncture strength and less susceptibility to clogging or blockage of the bore-hole. Such a structure in some applications and using some materials can allow for other advantageous needle characteristics, such as a greater total shank height and/or greater diameter bore-hole, which can improve capillary flow.

Many different variations in shape or overall configurations are possible in accordance with specific embodiments of the microneedle with substantially off-center through-hole. Different applications, or materials, or fabrication methods may call for different specific dimensions, shapes or ratios than those described in the examples given herein. Generally, a microneedle with substantially off-center through-hole is characterized by having a substantially solid tip and a through-hole that is not completely open until well below the needle shaft apex.

For example, in specific embodiments, a microneedle according to this embodiment may have a substantially solid tip that comprises at least 20% of the total shaft height. In other specific embodiments, a microneedle according to this embodiment may have a substantially solid tip that comprises at least 40% of the total shaft height. In other specific embodiments, a microneedle according to this embodiment may have a substantially solid tip that comprises at least 60% of the total shaft height. In other specific embodiments, a microneedle according to this embodiment may have a substantially solid tip that comprises at least 85% of the total shaft height.

In some embodiments, a groove may result from manufacturing of the off-center through hole and extend from below the substantially solid tip to the completely surrounding top opening of the through-hole near the base. A groove according to specific embodiments of the invention can provide a number of advantageous, one being that the recessed channel of the groove provides a location for fluid transfer that is somewhat protected from blockage of cellular bodies.

Microneedle with substantially off-center through-hole may be further understood by consideration of specific example embodiments. Discussion of these embodiments may include details, dimensions, or materials that are given as examples only, and thus the invention should be considered not limited except as described in attached claims.

Figure 2:
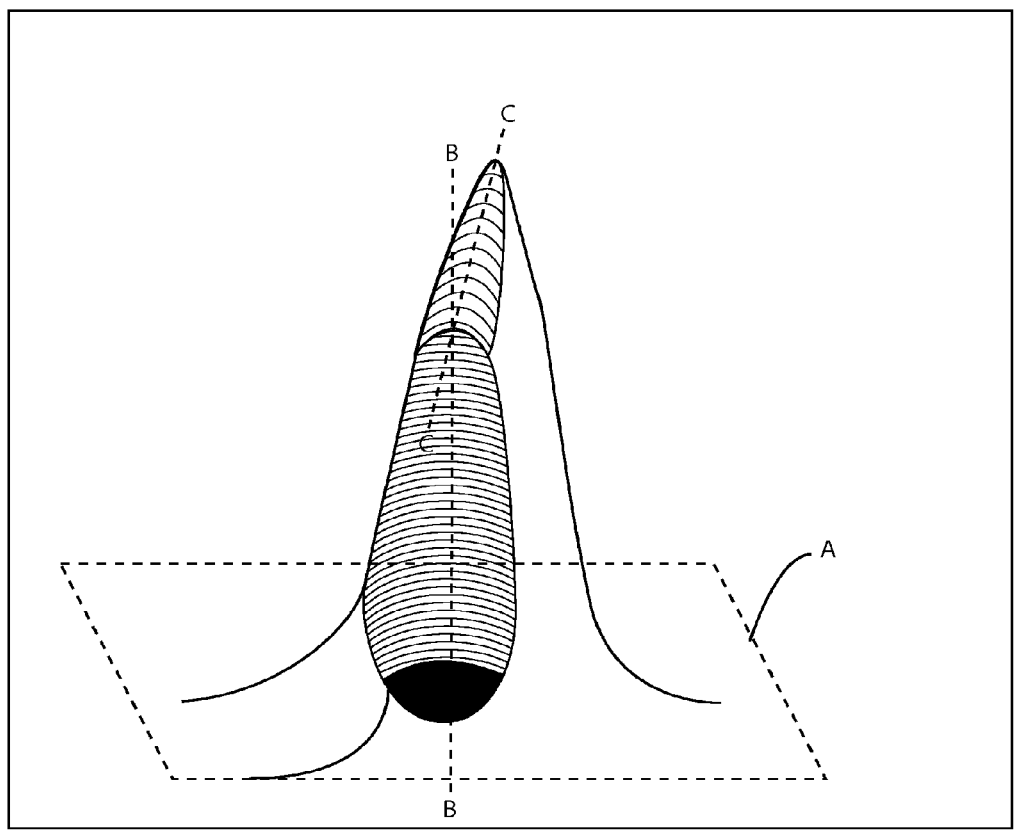
FIG. 2 is micrograph of an example snake-fang microneedle tip according to specific embodiments of the invention.

FIG. 1 is an illustration of an example snake-fang microneedle array according to specific embodiments of the invention. FIG. 2 is micrograph of an example snake-fang microneedle tip according to specific embodiments of the invention. These particular example needles were fabricated using an isotropic etch of roughly squared columns with an off-centered through-hole in an etchable substance, such as doped silicon, undoped silicon, or some glass or metals. The etching fabrication of particular materials provides a characteristic rounded shape to the microneedle. Various details of one example etching fabrication method are described further below.

This illustrated embodiment furthermore includes a groove 10 defining a groove line C extending from somewhat below the needle tip 20 down to the completely opened through-hole 30 (where completely-opened can also be understood as a hole that is completely surrounded by solid material in a plane A roughly perpendicular to the needle shaft, the shaft roughly parallel to vertical line B) that is near the base 40. The groove forms an acute angle with vertical line B. While this groove is optional, in some embodiments it may provide further benefit in guiding fluid flow. As described above, the recessed portion 11 of the grove 10 is somewhat protected from blockage by cellular bodies. Furthermore, the rough surfaces of the grove, which can be achieved by using a DRIE process for forming the off-center through-hole, provide increased surface area that increase capillary fluid flow.

As a result of the characteristic shape of this example embodiment, this microneedle configuration is referred to at times as a snake-fang micro-needle or cobra-fang microneedle. At other times, snake-fang can be understood to refer to any microneedle with a substantially off-center through-hole.

Figure 3:
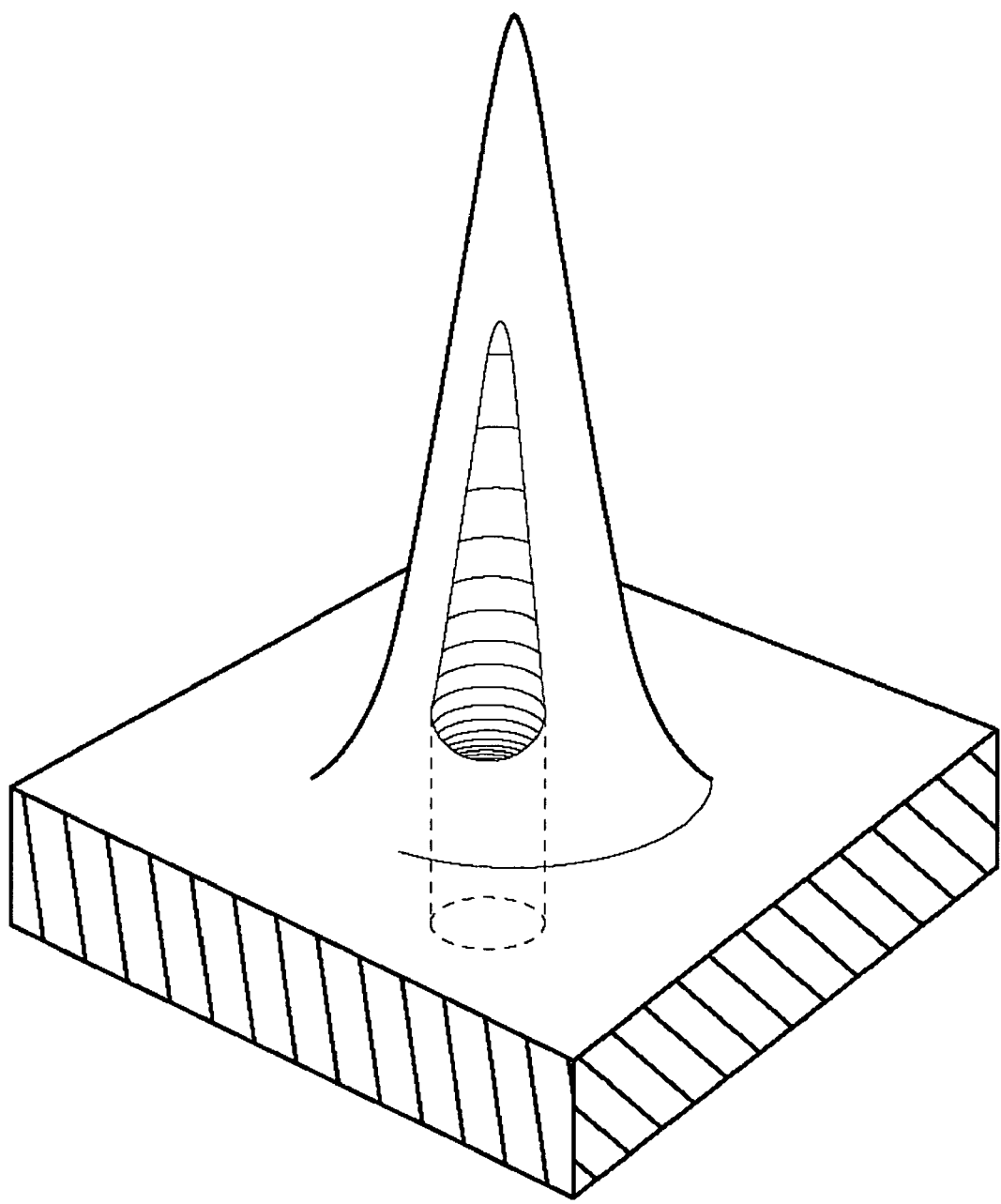
FIG. 3 is schematic diagram of a first example snake-fang microneedle tip according to specific embodiments of the invention.
Figure 4:
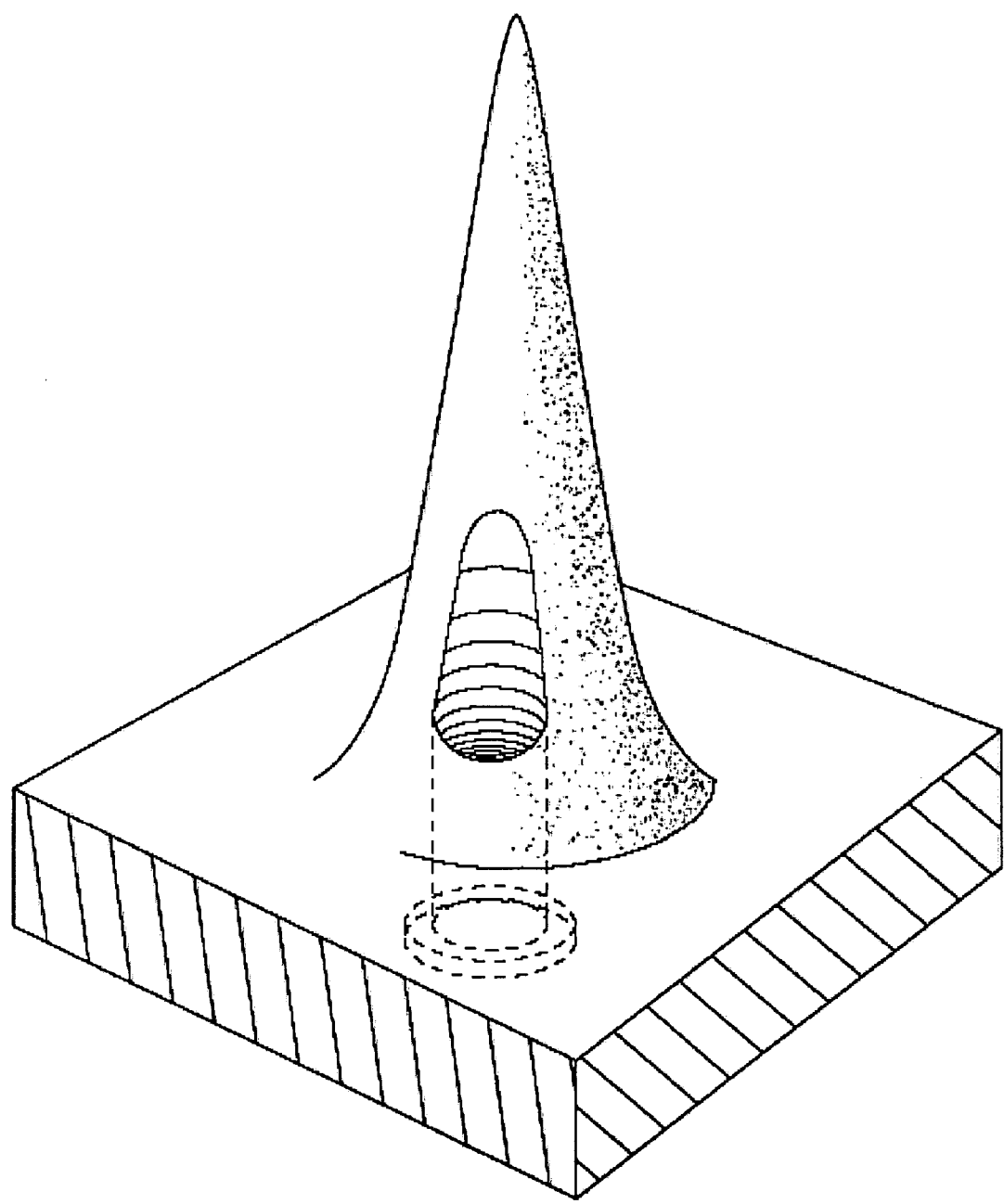
FIG. 4 is schematic diagram of a second example snake-fang microneedle tip according to specific embodiments of the invention.

Other configurations of off-center through-hole microneedles can include microneedles that are more nearly conical shaped, such as shown in FIG. 3 and FIG. 4, which are schematic diagrams of different configurations of off-center through-hole microneedles. In needle systems, generally a via connects from the hole at the base of microneedle to a backside channel or reservoir, allowing unobstructed fluid flow through to the collecting channels or reservoir on the backside of the device. Regular or irregular pyramid shaped configurations, also including an off-center through hole and partial groove, are also possible and may be desirable in specific application or fabrication embodiments.

Microneedles with substantially off-center through-holes can be made to have extremely sharp, solid tips able to withstand repeated skin penetration without breakage. Furthermore, hole plugging problems that can occur in very small needles are substantially reduced as a result of the solid tip design. Any suitable material can be used to fabricate such a microneedles using any appropriate fabrication method. One example fabrication method for forming needles in silicon or other etchable material is discussed further below.

A wide range of dimensions and arrangements of multiple needles are possible using this needle design. For human external use, one investigated needle height is approximately 100-400 microns in shank height, with needles arranged in arrays of between about 50 and about 2000 microneedles. However, in many applications, very different dimensions will be desired. For example, much taller needles may be desired for large animal applications, such as bovine or porcine, or sampling fluid from larger plant structures. Conversely, shorter needles may be desired for small animal applications, or small plant structure sampling, or other uses.

One tested material and dimensions involved arrays of snake-fang microneedles fabricated in silicon using well-known micro-fabrication techniques. One example array consisted of about 400 microneedles, fabricated from single crystal silicon to a shank height of 250-350 microns with 300 microns center-to-center spacing, where the through-holes were off-centered in the needle column approximately 50 microns, or about 16% of the center to center spacing. These example silicon microneedles have extremely sharp, solid tips that were able to withstand repeated skin penetration without exhibiting any tip breakage or damage or substantial bore hole plugging problems.

Micro-Hypodermic Microneedle

Figure 5:
FIG. 5 is a micrograph of an example hypodermic microneedle array according to specific embodiments of the invention.
Figure 6:
FIG. 6 is a micrograph of an example hypodermic microneedle tip according to specific embodiments of the invention.

A Micro-Hypodermic Microneedle is achieved by off-centering the borehole inside the needle body, though not so much as in the previous configuration. FIG. 5 is a micrograph of an example hypodermic microneedle array according to specific embodiments of the invention. FIG. 6 is a micrograph of an example hypodermic microneedle tip according to specific embodiments of the invention. This design can create extremely sharp (2 microns radius of curvature in specific example embodiments) microneedles. Penetration experiments revealed no tip damage. The tip of the micro-hypodermic needle is semi-solid, providing the necessary mechanical strength for penetration through the stratum corneum without chipping. With this design, the needle tips can be sharpened to a very fine point (in contrast with the "Volcano" design) so that they pass into the stratum corneum generally between cells, pushing the cells apart, rather than cutting or tearing them, creating very little tissue damage. While this may be a preferable design in some applications and some dimensions, plugging problems can occur. Although the borehole was elongated along the side of the needle, this design exhibited some bore hole plugging problems, in similar fashion to the volcano-like design.

Volcano-Like Microneedle

Figure 7:
FIG. 7 is a micrograph of an example volcano microneedle according to specific embodiments of the invention.
Figure 8:
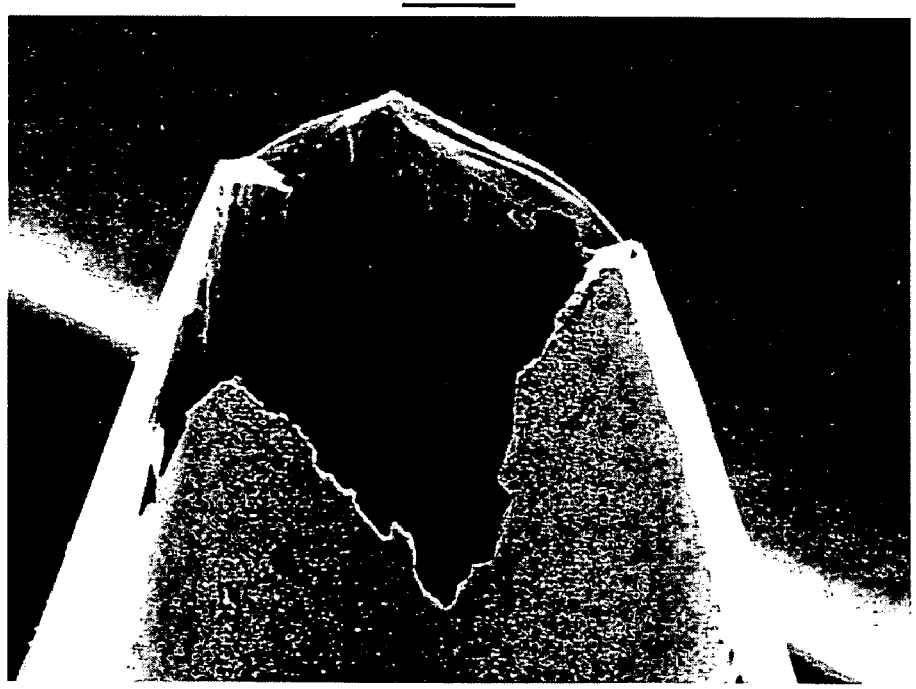
FIG. 8 is a micrograph of an example volcano microneedle tip according to specific embodiments of the invention.

An alternative volcano-like design is achieved by centering the borehole inside the needle body, e.g. a silicon column before etching. FIG. 7 is a micrograph of an example volcano microneedle according to specific embodiments of the invention. FIG. 8 is a micrograph of an example volcano microneedle tip according to specific embodiments of the invention. Very accurate placement of the borehole was needed to achieve the desired conical shape in specific embodiments. (Example dimensions are ~10-micron diameter hole and ~130-micron square silicon column). Therefore, photolithographic patterning and DRIE etching of the columns was necessary prior to glass bonding. In one example fabrication system, this limited the achievable height of the needle shanks to 200 microns before the wafer would become too fragile for handling.

One difficulty with this design for small needles is that at the tip of the microneedle, the walls around the bore opening can be thin and relatively fragile, (e.g., a widened 15-micron bore hole with 3-5 microns thick walls). Skin insertion tests indicate that failure of the walls can occur, effectively widening the bore opening and shortening the overall height of the microneedle. In addition, the centered bore can act as a punch, becoming blocked with tissue that can prevent transdermal fluid transfer. Thus, while this design for 100-200 micron needles for human applications is less preferable, in some applications or with different dimensions or materials, this can be an effective design.

Mechanical Failure Considerations

Failure modes for a micro-needle fabricated from single-crystalline silicon, silicon, or other partially rigid material are buckling, crushing, and shearing during loading as well as tensile rupture during unloading. Buckling occurs during epidermal insertion of the micro-needles, when the axial reactive skin force through the centroid of the shaft causes the shaft to "sag" or bend out of plane with respect to the needle length. The second method of failure is crushing in compression. Crushing will be the prominent failure mode when the shaft is short enough not to buckle. Shear fracture is another force of concern in needle insertion.

Two-dimensional (2D) microneedle arrays can withstand higher applied force than individual needles or one-dimensional array designs because of the distribution of forces, both normal and shear. Out-of-plane needle designs facilitate the fabrication of 2D arrays, and the application of normal forces to the needles during insertion. If the shear force during epidermal penetration is great enough to break a needle (typically at the base), the wedge cone shape of the needles provides a surface onto which contractions of the skin during normal movement produces sufficient force on the needle shafts, normal to the skin surface to push the needle out of the skin, much like a splinter. In addition, when pressed onto the skin, a 2D array stretches the skin between tips, making it less likely to fold around the tip, making the skin easier to pierce. An additional benefit of a 2D array is that a large, overall, needle shank surface area produces self-adhesion by friction when inserted into the elastic skin, minimizing the need for additional fixtures to hold the needles in place. Application of a strip of adhesive tape is generally all that is required to affix the needle array in place and protect it from dislodgement during activity.

Snake-fang needles according to specific embodiments of the invention were particularly resistant to breakage due to any of these forces when used for human skin insertion.

Through-holes With Staggered Diameters

Creating a hollow bore or through-hole in a microneedle for the transfer of fluids in specific embodiments is a challenging problem of size. With example microneedles that have a tip to base aspect ratio of 1:50 (e.g., 2 microns at the tip and 100 microns at the base), the median diameter of the needles occurs only 50 microns from the base of the needle. Due to this apparent limitation of needle geometry, a borehole generally cannot exceed 10-20 microns in diameter in many materials, otherwise the side walls of the needle can become too fragile for cutaneous penetration.

Though in silicon, a single hole etched through the substrate (e.g., by DRIE) is an attractive method for creating the bore-hole, in some embodiments the limitations of this method can lead to a hole diameter so small that the surface tension forces normal to the flow of fluid are larger than the capillary force parallel to the fluid flow. In this case, fluid flow without external force gradients would not be possible. The fluid would remain near the tip of the needle, potentially unable to enter the full length of the borehole or underlying microchannels or reservoir without substantial pumping or prefilling, which could complicate device design or usage.

However, if the diameter of the boreholes is too large, two problems are encountered. First, as mentioned above, the walls of the needle can become too fragile for epidermal penetration. Second, the viscous drag forces of the fluid (due to increased fluid volume) may become greater than the forward capillary forces generated by surface tension and the fluid would not be drawn into the borehole and subsequently into the microchannels.

Therefore, in particular example embodiments, different through-hole diameters are used at the base of the needles and at the tips. In specific embodiments, a target diameter of the borehole is chosen as about 30 to 40 microns at or below the base of the needle connected to about a 10-micron through-hole nearer to the tip of the needle or on the needle shaft. This combination structure allows for a small opening on the microneedle and provides a large enough patterned hole diameter near or below the base of the needle to obtain sufficient etch depth, creating a through hole.

4. Materials

In specific embodiments, the device is fabricated from one or more of silicon, silicon nitride, platinum, titanium, and glass. Other embodiments can use polymer materials, ceramic materials, or any materials that can be molded, etched, punched, or otherwise fabricated or grown to form a needle of the desired configuration at the desired dimensions.

A number of different methods are known for forming microneedles and a variety of these methods and different types of microneedle arrays can be used in a device according to specific embodiments of the invention. One such device is described in B. Stoeber, D. Liepmann, Method of Forming Vertical, Hollow Needles within a Semiconductor Substrate, and Needles Formed Thereby, U.S. Pat. No. 6,406,638, Jun. 18, 2002. Microneedle arrays built using plastic and metal technology can also be used in a device according to specific embodiments of the invention.

While etched microneedle designs have been the most studied so far, other methods for forming microneedles can also be employed according to specific embodiments of the invention.

According to specific embodiments of the invention, biocompatibility of the materials used in constructing the microneedles is a concern since the needles in some embodiments can penetrate the stratum corneum and reside in the living layers of the epidermis and dermis. Experimental results suggest that silicon, silicon nitride and titanium are "non-irritants" in one and twelve week studies using in vitro models.

While glass may be used in some embodiments of a microneedle according to the invention, assuming the overall structure to be the same as a silicon micro-needle, the buckling force for typical silicon dioxide micro-needle is generally about ⅓ that of silicon. This translates to a buckling force for glass that is lower than the calculated forces necessary for skin penetration. Therefore buckling failure would occur. For this reason, glass as the primary needle material is not at present a preferred embodiment for needles of many of the example dimensions described herein. However, different glass compositions or manufacturing techniques can provide glass with more desirable strength characteristics.

5. Example Needle Array systems

Microneedles as described above can be used in a wide variety of applications, including integrated systems for in situ monitoring, analysis, or substance delivery. In order to characterize some aspects of such systems, a specific embodiment experimental system is described. Specific aspects of such a system are described for the purpose of completeness of disclosure and to disclose other novel aspects according to specific embodiments of the invention. However, novel microneedles as described herein can be used in a wide variety of systems, including systems including active pumping, electronics, and other structures not included in the examples provided below.

An example integrated microneedle array and microfluidic channels/reservoirs consists of a silicon/glass bilayer chip. FIG. 9 illustrates one example of a complete transdermal fluid transport device with approximately 400 microneedles and other components according to specific embodiments of the present invention. One goal of this example system was simplicity of design and ease of use and thus the system was designed in part to enable capillary uptake of fluid. Overall example dimensions of approximately 2 cm×1 cm×0.1 cm provide one example of a system suitable for some human treatment and/or diagnostic applications, with each needle of about a 20×20 microneedle array consisting of an about 200-400 micron tall needle shaft with about a 120 micron base diameter on about 300 micron centers. In one example device, uptake of minute fluid samples takes place within an off-center, needle borehole of 10-15 microns in diameter in as few as 10% of the 400 microneedles or up to 100% of the needles per chip. A reservoir for the fluid collection is connected to multiple hollow needles on the backside of the silicon wafer, opposite the needle tips, by one or more microchannels.

An anodically bonded Pyrexm™ glass cap seals the channels and enables visual inspection during and after filling. In order to access the reservoir, 4 mm holes can be provided in the glass cover, prior to bonding, for example using a diamond coated drill bit. Because the device can be partially made as a batch process, the processing time and associated expense is decreased making the device cost effective.

Design

Four main structures comprise an example transdermal fluid transport device: microneedle, borehole, microchannel and the microneedle/microchannel interface. Each of these components is defined by individual processing steps, which generates a large degree of freedom in designing the entire chip as a system.

In an example system, degenerately doped silicon was utilized for the main part of the microneedle, since the fabrication process was well characterized. An added benefit of using silicon in this example design, as opposed to glass or plastic, is that the process of glass/silicon bonding was also well characterized. Thus, the two substrates chosen for the fabrication of integrated hollow microneedles and microchannels in a specific example system were silicon and PyrexTm™ 7740 glass. Visualization of fluids extracted by the microneedles was desirable in experimental systems, so microchannels with a transparent window were used. Pyrex 7740 glass was also chosen as a means to mechanically strengthen the device against the force of epidermal penetration, though for that purpose, any number of materials are possible.

Since both silicon and glass can be micromachined, both are candidates for channel formation. Integration of electronics for fluid movement, concentration and analysis in the microchannels suggests that the microchannels should be fabricated in the glass substrate as glass channels allows for successive micromachining of integrated circuitry on (and in) the silicon substrate since the polished silicon surface would be conducive for photolithography.

However, difficulties in producing compensation structures for fluid uptake in glass microchannels led to fabrication of the microchannels in the silicon substrate in this example system. Using photolithography to define the microchannels also allowed fluid from individual channels to be collected into a photolithography defined integrated reservoir for analysis. An added benefit of silicon microchannels was that the glass remained continuously flat therefore, it was transparent to visible light without the need for polishing or surface treatments.

Capillary Draw (Compensation)

Filling a hydrophilic micro-capillary by a Newtonian fluid is governed by surface tension, which relies on the imbalance of intermolecular forces at an interface. The forces (van der Waals-dipole/dipole interactions, London dispersion-fluctuating induced dipole, and hydrogen bonds) all contribute to changes in surface tension at the interface. To maximize the capillary force, the contact angle must be minimized. For polar liquids, involving water and blood, on a silicon dioxide hydrophilic surface, the contact angle is <90°. This contributes to a positive $\cos(\theta)$, which indicates that the solid/liquid interface surface tension is lower than the solid/gas surface tension and drawing the fluid towards the gas/liquid interface of the capillary. In order for the liquid entering the needles to connect with microchannels on the backside of the chip, the fluid exiting the bore from the distal end of the needle must make a 90° turn in this example system.

One solution to compensate for this problem is to provide a continuous surface beyond the opening to the backside channel, as illustrated in FIG. 10B. (FIG. 10A illustrates a structure without compensation.) The outlet from the needle is thus configured so that a portion of the exit hole wall extends to contact a covering material at the base side of the needles (e.g., the glass lid.) This geometry provides enough capillary force to draw fluid from the outlet of the microneedle, pass the 90° turn and proceed into the backside channel where surface tension draws fluid into the channel. Since these compensation structural can be difficult to create in glass is some fabrication situations, one solution is to fabricate the channels in the backside of the silicon column array. By surrounding roughly three sides of an exit hole with a continuous (e.g. silicon oxide) surface, filling the microchannels by capillary action is achieved.

Integration of micromachined valving, pumping and electronics for separation, concentration and analysis of biomolecules can also be included in the device in specific embodiments, using a variety of known microfabrication processes. The device can thus be embodied as a self contained unit attached to the skin, extracting biological fluid samples, analyzing the contents and administering the appropriate chemicals to keep the body in homeostasis: a portable health monitor.

6. Operational Experiments

Skin Puncture Test

Confirmation of skin piercing by microneedles as described above was achieved with a handheld in vivo confocal microscope. These experiments confirmed that a microneedle array according to specific embodiments of the invention can pierce through the highly protective stratum corneum and into the living sublayers. After repeated pressing of the chip into human skin (>20 times), there was no evidence of tip breakage or other damage to the needles when examined in both optical and electron microscopes. A contributing factor for this is the large number of needles, most of which are solid is specific embodiments, making up the array. The needles distribute the shear forces experienced while pressing the device through the compliant skin. The amount of pressure needed to pierce the skin was measured using an ordinary laboratory digital scale to be 1.5 N±0.25 N, which is similar to the force typically needed to adhere a Band Aid® to the skin.

Fluid Filling Demonstration

Capillary filling tests were performed using a wide variety of both non-biological (glycerol, acetone and DI water) and biological (blister fluid, surrogate interstitial fluid, interstitial fluid and whole blood) liquids. All fluids were successfully drawn into the microchannels immediately upon touching the needle tips to the surface of the fluid. Individual red blood cells can be clearly seen with the aid of a microscope.

(Interstitial Fluid) Extraction From Skin

A snake-fang microneedle array according to specific embodiments of the invention was used to successfully extract ISF from skin, with less susceptibility to blockage due to skin plugging during cutaneous penetration that the hypodermic needle. A snake fang microneedle array was used in a test on a human earlobe held in place with a spring clip for 15-20 min, and a clear fluid with no visible cellular matter collected in the backside channels of the micro-device after extraction. In order to confirm the presence of ISF, and not some other fluid, e.g. sweat, an in situ detection of glucose was made using a commercial blood glucose test strip which confirmed approximate glucose concentrations in the extracted fluid of those in the subject's blood.

In specific example systems, an initial 20-30 min latent time was needed to generate enough ISF to fill the borehole of the microneedle and the backside channels, however evaporation at the distal opening above the reservoir maintains the pressure gradient allowing continuous capillary draw of the fluid. Other techniques, such as prefilling the microneedles, can reduce this latent time.

7. Fabrication

Many different methods for fabricating microneedles have been proposed and are known in the art. These include various etching techniques, molding, punch, stamping, and etc. and various combinations of methods. Any of these methods can be used to construct microneedle and microneedle arrays as described above. However, in order to provide a complete description and by way of example, some specific examples of microneedle fabrication are described below. Some of these specific examples use methods that are familiar from semiconductor device fabrication and/or methods known or described in referenced documents for the fabrication of microneedles. These methods benefit from the wide availability of systems, materials, and expertise that are compatible with such fabrication. In specific embodiments, methods of fabrication are employed that by varying certain parameters but otherwise using the same series of fabrication steps and photolithographic masks, provide for a wide range of needle sizes and shapes that can be custom built for different applications, including the shapes and sizes discussed above.

Descriptions of example methods provided herein generally do not include all steps and details of processing that are well know in the art. In particular, in some instances, processing times, specific materials used, processing temperatures, etc., will vary based on the particular fabrication systems available. The setting of such parameters for particular systems to achieve described results is well known in the art and within the skill of the ordinary artisan. Thus, the below description concentrates on details of example processing steps that may be less familiar in the art or are unique to the present invention. Furthermore, any specific parameters and/or dimensions provided below are examples of specific embodiments and should not be read to limit the invention.

In specific embodiments, a combination of Deep Reactive Ion Etching (DRIE) and isotropic etching is used to produce out-of-plane, hollow microneedles and optionally also integrated microchannels and/or reservoirs at the base of the microneedles. Anodic glass/silicon bonding can optionally further be used to seal the chambers and channels and to provide additional structural strength to the silicon substrate. Independent control of the hole size, needle height, shape and spacing is achieved by means of a separate process step for each parameter, such that a very wide range of geometries are achievable with the same fabrication process, and even with the same mask set.

Figure 11:
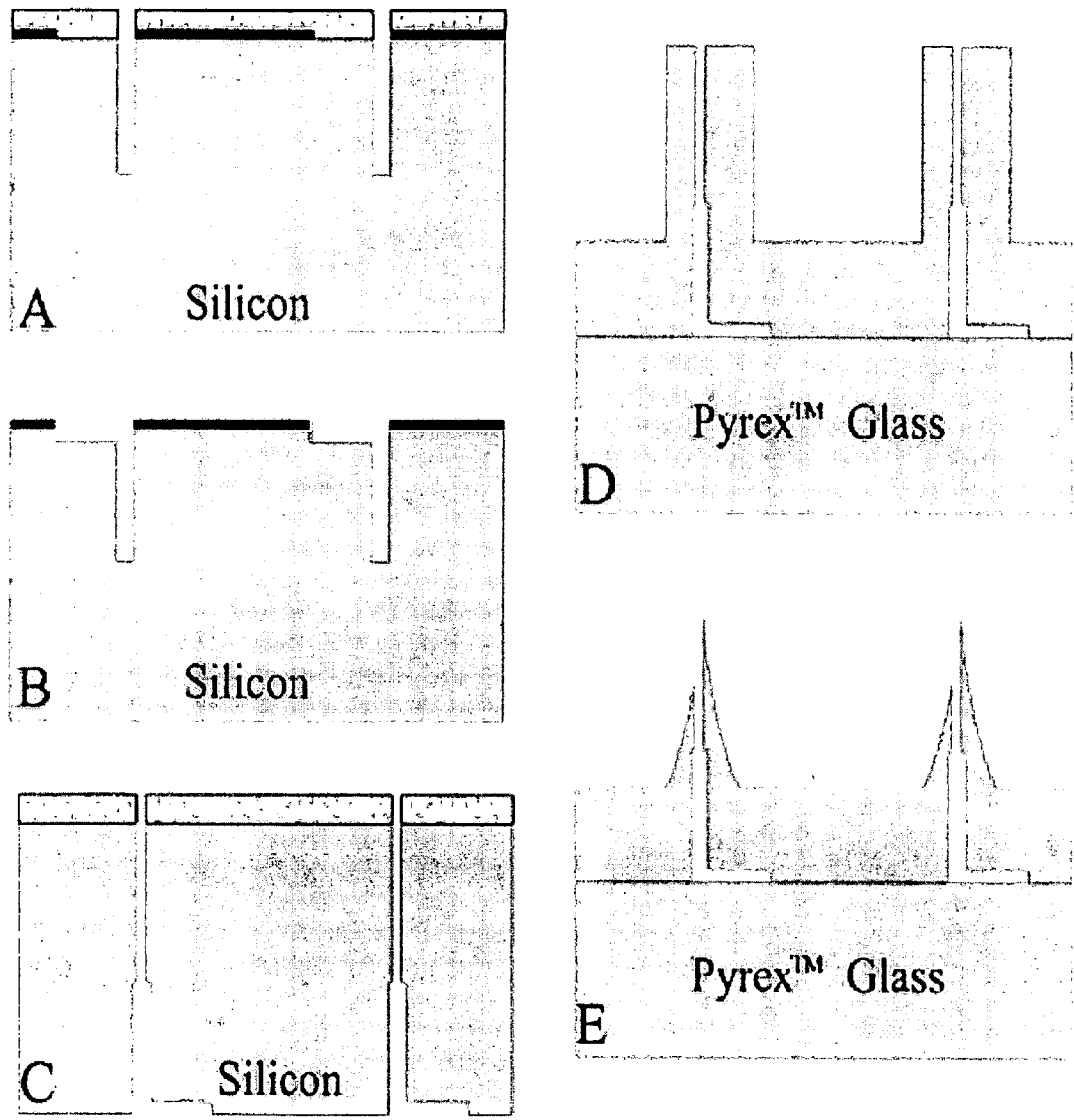
FIG. 11A-E is a schematic diagram illustrating fabrication of a microneedle array with bore-holes and reservoir channels according to specific embodiments of the invention.

FIG. 11 is a schematic diagram illustrating fabrication of a microneedle array with bore-holes and reservoir channels according to specific embodiments of the invention. This represents one example method that utilized a bonded glass or similar substrate for support during some fabrication steps and as part of microneedle systems.

Initial Substrate Handling

As an example, low resistivity (about 0.01 Ohms-cm), p-type, single-side-polished silicon wafers were used as the starting material for microfabrication. The orientation and wafer diameter are not critical, but the wafer thickness in specific example embodiments is limited by the maximum aspect ratio of etching achievable with available DRIE. As an example, and to be compatible with particular manufacturing equipment, the starting material was a four-inch diameter, single-side polished silicon wafer, with thickness of 500 microns, and (100) crystal orientation.

Channel Fabrication

In this example fabrication, the "backside" of the wafer (polished side) is first coated with a material to allow patterning of channels. In one embodiment, thin film aluminum is used, though in other embodiments different coating materials and/or no coating are possible. In some microneedle embodiments, microchannels and/or reservoir are photo patterned and etched on the coated side of the wafer in order to provide a reservoir for fluid flow either into or from the microneedle tip or for prefilling of microneedles. (FIG. 11 dark bar indicates aluminum or other suitable patternable coating.)

Backside Through-holes

Photoresist or some other appropriate second coating is patterned on the backside of the wafer to open the about 30 microns holes aligned to the previously defined channel structures. (FIG. 11A, spotted material.) The patterned holes are etched into the silicon substrate, for example by DRIE (for example, using a Surface Technologies Systems ICP etcher and the Bosch™ process to a depth of 360 microns.) After stripping the photoresist, the channels and reservoir patterns are etched into the silicon substrate, using the previously patterned coating (again, e.g. aluminum) as a mask, to a depth of about 15-20 microns, for example using RIE. (FIG. 11B.) The remaining coating is removed, for example using a PAN etch. (FIG. 11C, lower surface.) Aluminum is useful as an alternate masking material when the etch rate selectivity is reduced. In one example, 1000 Å of aluminum was deposited onto a bare silicon wafer.

Alternatively to using aluminum as the etch mask coating, a thin layer of silicon dioxide (1500 Å) can be placed on the bare silicon wafer surface (e.g., by thermally growing) in some embodiments to facilitate creating the necessary channel structure surrounding a DRIE via hole. The silicon dioxide can be patterned for channel fabrication using standard photolithographic processing followed by a wet chemical silicon oxide etch, also known as Buffered Oxide Etch—BOE. The silicon dioxide can be used as an etch mask for the DRIE to create the final channel structures after the holes were etched, in some embodiments. A relatively uniform layer of AZP 4620 thick photoresist can be spun and patterned over the thin silicon oxide layer and used as an etch mask for the DRIE. Once etched, the thick photoresist is removed, leaving the aligned silicon dioxide mask for subsequent channel formation. The etch rate selectivity between silicon and silicon oxide is 100:1. Since the final desired depth of the channels in this embodiment was about 15 microns, the 1500 Å of silicon oxide was sufficient as an etch mask.

Frontside Through-holes

"Frontside" needle boreholes were defined using a mask aligner (e.g., a Karl Suss Backside Mask Aligner) in thick photoresist (5-10 microns), (FIG. 1 IC, upper surface.). The "as patterned" square hole diameters were approximately 10 microns across and are aligned to both the previously defined channel structures and to the 30 micron holes on the opposite side of the wafer. These smaller holes are etched into the silicon substrate, for example using DRIE, until they connect with the holes extending from the opposite side, at an approximate depth of about 170 microns, with vertical/lateral etch aspect ratio of approximately 25.

Removing the patterned photoresist from the wafer leaves a clean surface for anodic bonding of a second support layer (e.g., Pyrex 7740™ glass lids) at the base side of the micro needles.

Column Formation and Sharpening

The microneedle shanks are defined by first forming columns in the silicon (FIG. 11D) followed by sharpening of the columns.

Figure 13:
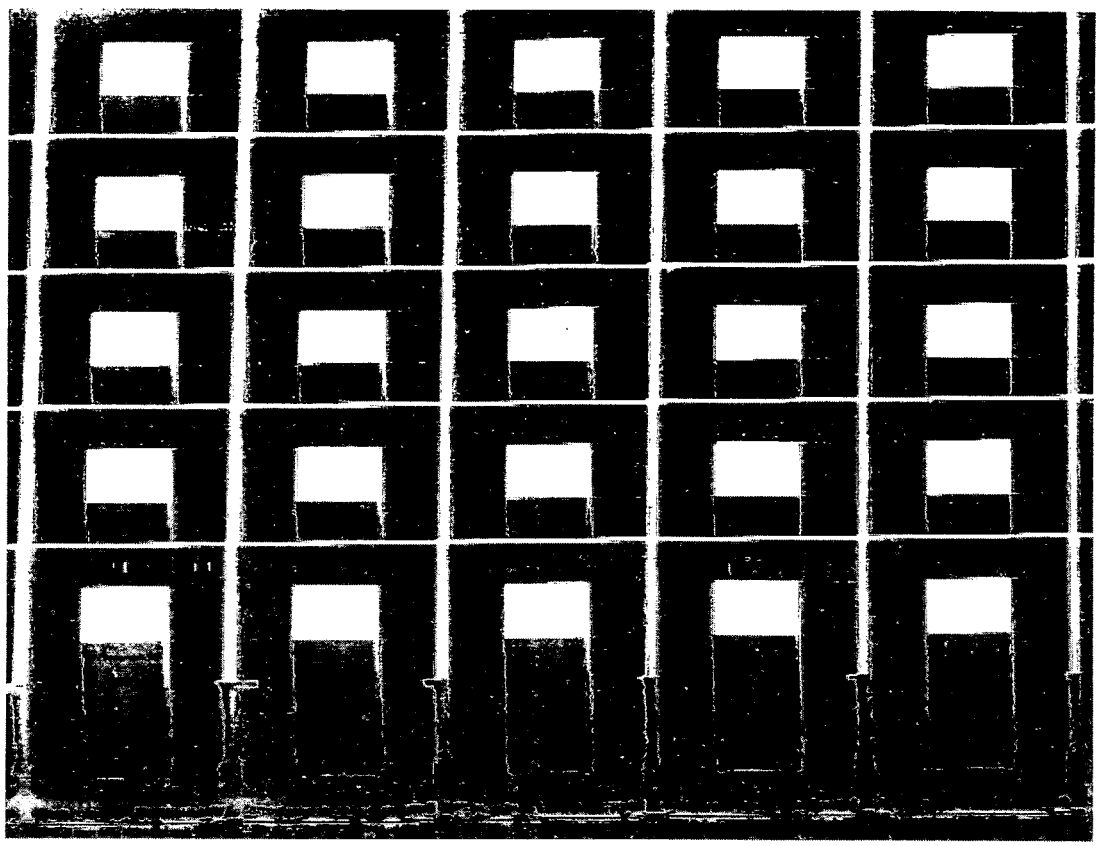
FIG. 13 is a micrograph of an example of columns formed in a substrate using DRIE and before further etching to form needles according to specific embodiments of the invention.

Pre-needle columns can defined using DRIE, which provides columns that can be photolithographically aligned within 10-20 micron of the single hole using an infrared OAI backside aligner. With this aligner, 150 micron×150 micron pre-column areas were aligned to the 45 micron holes from the opposite side and were patterned in thick photoresist. DRIE formed columns generally may improve yield and create a better alignment between the columns and the borehole. FIG. 13 is a micrograph of an example of columns formed in a substrate using DRIE and before further etching to form needles according to specific embodiments of the invention. In this example, the walls are left surrounding each column after the DRIE. These walls are etched away during the needle sharpening.

Alternatively, an automated dicing saw can be used to form the columns rather than DRIE in specific embodiments, for example in order to achieve needle shank heights of >200 microns when DRIE systems are not available that can etch the desired materials to that depth. This was done in an example fabrication method because the supporting glass substrate proved difficult inside the DRIE chamber and without the supporting glass, a DRIE etched silicon substrate may be too fragile for further processing. However, the accuracy with which one can position the borehole within the column is crucial to achieving a desired needle tip shape as described below, and this accuracy may require high-precision saws in some situations.

Sharpening can be performed for example using an isotropic, silicon etchant composed of hydrofluoric, nitric and acetic acids. This etchant, commonly called HNA, has a fast, yet very reproducible etch rate of degenerately doped, p-type silicon. Alternating between an agitated and quiescent phase, the silicon columns are thinned and sharpened into needles. The characteristic shape of the needles is produced by the localized limited diffusion of the etchant during the quiescent phase.

Specific Example Column Formation

In one embodiment, formation of the pre-needle silicon columns was accomplished by removing excess silicon by means of a dicing saw. Using a 6 mil wide, 30 micron diamond grit resin dicing blade mounted in a 30 mil exposure hub, a 21×21 matrix of cuts, 200-400 microns deep on 300 micron centers created an array of 400, 140 micron square columns, 200-400 microns tall.

The position of the borehole was paramount to the final shape of the hollow microneedle. Control of hole position was accomplished by alignment of the dicing cuts during columns formation. An important note was that before each set of cuts, the actual height of the glass/silicon surface must be measured. Therefore, starting 100 microns higher than the theoretical total height of the silicon/glass bonded pair, successively deeper cuts were made on the edge of the silicon surface until the sawing marks were visualized. This sets the actual height of the silicon surface. Once the columns were made, a final structure consisting of a 6 mm×6 mm array of columns surrounded by silicon fins was created. The fins were a by-product of the dicing and were necessary for uniform column etching. Without the fins, non-uniform flow of the etchant enhances etching of the columns near the edge of the array. Since the columns were created after the silicon nitride capping material was deposited, the capping material was localized to only the tops of the silicon columns.

Forming Different Needle Tip Shapes

Different needle tip shapes, such as those discussed above, can be produced by changing the relative positioning of the central bore hole to the shaft of the needle. This can be further understood be reference to FIG. 11D, which shows boreholes offset for a hypodermic microneedle. With the following dimensions provided as examples only, the "volcano-like" design is achieved by centering 10-micron borehole inside a 130-micron square silicon column.

For a "micro-hypodermic" design, the borehole was shifted 25 microns from the column's center, which created extremely sharp (2 microns radius of curvature) needles. Penetration experiments revealed no tip damage. The tip of the micro-hypodermic needle is semi-solid, providing the necessary mechanical strength for penetration through the stratum corneum without chipping. With this design, the needle tips can be sharpened to a very fine point (in contrast with the "Volcano" design) so that they pass into the stratum corneum between cells, pushing the cells apart, rather than cutting or tearing them, creating very little tissue damage. Although the borehole was elongated along the side of the needle, this design also exhibited some bore hole plugging problems, in similar fashion to the volcano-like design.

A snake-fang design using this fabrication method shifted the borehole an additional 25 microns (50 microns total) from the center of the column. This shift resulted in a cobra fang-like structure consisting of a solid micro-needle. A groove extending from somewhat below the needle tip down to the base aided in fluid flow in specific embodiments. The via hole to the backside channels connects to the base of the groove allowing unobstructed fluid flow down the groove to the via hole and through to the collecting channels on the backside of the device. These microneedles have extremely sharp, solid tips that were able to withstand repeated skin penetration demonstrations without exhibiting any tip breakage or damage.

Through-Hole Considerations

Fluid transport from living tissue requires: 1) penetrating the stratum corneum for gaining access to living tissue, as provided by various microneedle structures described above; 2) a method for transporting fluid to and from the living tissue; and 3) structure for fluid transport confirmation and analysis. The second prerequisite involves a structure that allows fluids to flow by creating a pressure gradient or capillary force to and from the living tissue.

Etching a small hole through the silicon wafers from one side and creating a column around it from the opposite side is in theory very simple, requiring a single photolithographic step to define the holes. While this may be a preferred method in some embodiments, it has been found that at present using available fabrication techniques, a two-hole fabrication method provides a preferable result.

Two Sides, Aligned Bore-holes

In order to produce better alignment in some embodiments (e.g. when a dicing saw is used) and also to create a smaller opening on the topside or needle side of the wafer surface, fabrication using two holes from opposite sides of the wafer is utilized according to specific embodiments of the invention. Note that while a two-hole design is described in detail herein, the present invention in specific embodiments can also utilize a single-hole. As one example, an etched or stamped or molded hole from the bottom of the wafer may taper, so that a desired diameter is achieved at the base of the device, and a narrower diameter nearer the needle shank. In an example fabrication method, a patterned about 30 micron diameter hole was chosen for the "channel side". The needle side hole diameter is about 10 microns. Since the profile of one example DRIE etch was 25:1, etching the channel-side hole to a depth of 375 microns and etching the needle side hole to a final depth of 125 micron connects the two holes. Alignment of the holes was realized utilizing a MA6 Karl Suss Backside Aligner. This aligner uses an image grabbing system for alignment as opposed to IR transmission through the silicon wafer. No heat was produced and the alignment accuracies were within 1-2 micron back to front.

Microchannels in Glass or Silicon

Two options for creating backside channels for extracted fluid visualization and analysis were considered. Since visualization of the extracted fluid was the first task of the device, Pyrex® 7740 glass was chosen as the backing substrate. This glass not only created a sealing structure for the channels, providing a continuous surface for capillary draw as well as allowing viewing of any fluids drawn into the channels, but it also provided additional mechanical strength to withstand the forces of penetration during use.

Another option is whether to create the channels in the glass or in the silicon. Cutting channels into the glass using a dicing saw is one option that is quick and does not require any photolithography. However, compensation structures fabricated in the silicon substrate, opposite the microneedle array, were generally used to allow fluid to be draw into the channels.

Capping

Providing a cap at the top of the silicon columns aided in the uniformity of the needle height and shape. PECVD (Plasma Enhanced Chemical Vapor Deposition) silicon nitride was used in a specific embodiment for the cap, and generally was placed on the needle side of the wafer after through-hole formation, but before columns were formed. The caps on the tops of the columns protected the surface long enough to sharpen them (at which point the caps fall off) and helped produce needles of uniform height. FIG. 12 is a schematic diagram illustrating additional fabrication steps involving capping for forming microneedles according to specific embodiments of the invention.

An added benefit of silicon nitride and possibly other materials involved a thin layer that was deposited on the inside surface of the borehole. This provided protection against the silicon etchant and helped to provide a barrier from over etching of the sidewalls, maintained sufficient silicon of the sidewalls helping the device to mechanically withstand the forces of epidermal insertion. Other materials can be used for capping, such as photoresist, silicon dioxide, or other suitable material resistant to the etching process, but silicon nitride is a presently preferred material.

In specific embodiments, PECVD silicon nitride was used as the capping material to a final thickness of approximately 3000 Å. In one example PECVD silicon nitride was deposited at a rate of 120 Å/min using 50 sccm $NH_3$, 10 sccm $SiH_4$ and 40 W.

Conditioning Silicon Surfaces to Aid Fluid Flow

Although silicon oxidizes quickly in air to a "native oxide" thickness of 40 Å, the silicon surfaces benefited from conditioning to aid in minimizing the contact angle between the solid/liquid interfaces. This process slightly increases the silicon oxide thickness to help fluid transfer in the needle borehole and channels. Without this conditioning, fluid may move slowly into the channels and stops just after exiting the channel side borehole in specific configurations.

One example conditioning consists of soaking the complete chip in mixture of 1:1 nitric acid and hydrogen peroxide heated to 90 C. After soaking the chips for 1 hour, the ability to draw fluids into the channels through the boreholes is markedly increased. In addition, the chips can be reconditioned, following use to remove organic films deposited on the silicon surfaces through contact with biological fluids.

Other Example Fabrication details

In some applications, bonding surfaces where protected from extremely small (<1 micron) silicon particle during the sawing process that coat all surfaces of the wafer using photoresist baked on the polished side of the wafer prior to dicing.

8. Diagnostic Uses

As described above, following identification and validation of a sensor for a particular substance, including biological molecules such as sugars, proteins, fats, or any substance of interest according to the invention, in specific embodiments such detectors are used in clinical or research settings, such as to predictively categorize subjects into disease-relevant classes, to monitor subjects on a continuous basis to detect a substance of interest, etc. Detectors according to the methods the invention can be utilized for a variety of purposes by researchers, physicians, healthcare workers, hospitals, laboratories, patients, companies and other institutions. For example, the detectors can be applied to: diagnose disease; assess severity of disease; predict future occurrence of disease; predict future complications of disease; determine disease prognosis; evaluate the patient's risk; assess response to current drug therapy; assess response to current non-pharmacologic therapy; determine the most appropriate medication or treatment for the patient; and determine most appropriate additional diagnostic testing for the patient, among other clinically and epidemiologically relevant applications. Essentially any disease, condition, or status for which a substance or difference can be detected in an interstitial fluid can be evaluated, e.g., diagnosed, monitored, etc. using the diagnostic methods of the invention, see, e.g. FIG. 14, Table 1.

In addition to assessing health status at an individual level, the methods and diagnostic sensors of the present invention are suitable for evaluating subjects at a "population level," e.g., for epidemiological studies, or for population screening for a condition or disease.

Kits

A detector according to specific embodiments of the present invention is optionally provided to a user as a kit. Typically, a kit of the invention contains one or more sensors constructed according to the methods described herein. Most often, the kit contains a diagnostic sensor packaged in a suitable container. The kit optionally further comprises an instruction set or user manual detailing preferred methods of using the kit components for sensing a substance of interest.

When used according to the instructions, the kit enables the user to identify disease or condition specific substances (such as sugars and/or fats and/or proteins and/or anti-gens) using patient tissues, including, but not limited to interstitial fluids. The kit can also allow the user to access a central database server that receives and provides information to the user. Additionally, or alternatively, the kit allows the user, e.g., a health care practitioner, clinical laboratory, or researcher, to determine the probability that an individual belongs to a clinically relevant class of subjects (diagnostic or otherwise).

Thus, a microneedle-based system according to specific embodiments of the invention can be employed as an effective glucose monitor using a microneedle array and dialysis. Due to the optimum needle dimensions, it is sufficient to simply press the system onto the skin in order to reach the desired location in the epidermis with an abundant amount of interstitial fluid. The nerve endings are located deeper in the skin so that this procedure is painless. The glucose monitor can be attached to a skin location (for example, with a self-adhesive, medical tape, a band, etc.) by the patient himself without an assisted insertion procedure.

Other Embodiments

Although the present invention has been described in terms of various specific embodiments, it is not intended that the invention be limited to these embodiments. Modification within the spirit of the invention will be apparent to those skilled in the art. It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed is:

1. A microneedle comprising:
    a needle shaft with a solid tip, said shaft extending vertically above a needle base;
    said needle base defining a first plane (A) parallel to said base and said shaft defining a vertical line (B) substantially perpendicular to said first plane;
    an opening on said shaft, said opening being completely surrounded by solid material above said base nearer to said base than to said tip thereby forming a hollow microneedle;
    said opening having surrounding walls within said shaft that are substantially parallel to said vertical line; and
    a groove that runs along said shaft from said tip providing a recessed channel from said tip to said opening and terminates into said opening of said hollow microneedle, said groove defining a groove line (C), said groove at an acute angle from said vertical line;
    such that said tip can puncture a surface in order to deliver or sample fluids with reduced blockage of said opening, said opening being substantially distant from said solid tip, said groove providing fluidic guidance from said solid tip to said opening.

2. The device of claim 1 further comprising:
    said needle shaft is between about 100 to 5000 micrometers in height.

3. The device of claim 1 further comprising:
    said needle shaft is between about 100 to 450 micrometers in height.

4. The device of claim 1 further wherein:
    said opening comprises an off-center through-hole that is completely surrounded by solid material a substantial distance below said tip; and
    said groove extends from said tip to the top of the off-center through-hole wherein said groove allows for a greater total shaft height.

5. The device of claim 1 further comprising:
    said opening is surrounded on all sides beginning at least 60% below said tip on said needle shaft height and above said base; and
    said groove extends substantially from said needle tip to said opening.

6. The device of claim 1 further comprising:
said opening is surrounded on all sides beginning at least 90% below said tip on said needle shaft height and above said base; and
said groove extends from said needle tip to said opening.

7. The device of claim 4 further wherein:
said through hole becomes completely surrounded by solid material on said needle shaft in a plane roughly perpendicular to the needle shaft no more than 50% above said base.

8. The device of claim 1 further comprising:
said solid tip and said groove comprise at least 60% of said needle shaft height.

9. The device of claim 1 further comprising:
said solid tip and said groove comprise at least 80% of said needle shaft height.

10. The device of claim 1 further wherein:
said groove guides fluid flow between said tip and said through hole.

11. The device of claim 1 further comprising:
a substrate in contact with said base, said substrate providing support for said base, said hole extending into to said substrate to connect with one or more microchannels in said substrate.

12. The device of claim 1 further comprising:
a compensation structure between an underside hole of said needle and a channel floor, said structure easing fluid flow.

13. The device of claim 1 further wherein:
said opening is formed by etching.

14. The device of claim 1 further wherein:
said opening is formed by laser ablation.

15. The device of claim 1 further wherein:
said opening is formed using a mold.

16. The device of claim 1 further wherein:
said opening is formed using a drill.

17. The device of claim 4 further wherein a recessed portion of said groove is protected from blockage by cellular bodies.

18. The device of claim 4 further wherein said groove comprises a rough surface providing increased surface area that increase capillary fluid flow.

19. The device of claim 4 further wherein said groove comprises a recessed channel providing a location for fluid transfer that is somewhat protected from blockage of cellular bodies.

20. The device of claim 4 further wherein said off-center through-hole provides improved capillary flow.

21. The device of claim 4 further wherein:
said opening comprises an off-center through-hole that fully opens a substantial distance below the tip; and
said groove extends from said tip to the top of the off-center through-hole wherein said groove allows for a greater diameter bore-hole.

* * * * *